United States Patent [19]

Snider et al.

[11] 4,198,292

[45] Apr. 15, 1980

[54] PROCESS FOR METHANE AND AMMONIA EXTRACTION FROM ORGANIC WASTE

[75] Inventors: David R. Snider, Vincennes; J. Clifford Graham, Lafayette, both of Ind.

[73] Assignee: Graham-Snider Energy Systems, Vincennes, Ind.

[21] Appl. No.: 912,103

[22] Filed: Jun. 2, 1978

[51] Int. Cl.² .............................................. C02C 1/14
[52] U.S. Cl. ...................................................... 210/12
[58] Field of Search ................... 210/2, 12, 16, 10, 14

[56] References Cited

U.S. PATENT DOCUMENTS

| | | | |
|---|---|---|---|
| 3,338,826 | 8/1967 | Kramer | 210/12 |
| 3,981,800 | 9/1976 | Ort | 210/12 X |
| 4,040,953 | 8/1977 | Ort | 210/12 X |
| 4,076,515 | 2/1978 | Rickard | 210/16 X |

*Primary Examiner*—Thomas G. Wyse
*Attorney, Agent, or Firm*—Woodard, Weikart, Emhardt & Naughton

[57] ABSTRACT

A process for extracting methane gas and ammonia from raw material, such as organic waste. The process is carried out in a closed container or digester by anaerobic bacteria. The yield of the conventional anaerobic bacteria digestion process is greatly increased by the novel step of maintaining the space in the digester above the level of the raw material at a pressure below atmospheric during the digestion process.

1 Claim, 2 Drawing Figures

PROCESS FOR METHANE AND AMMONIA EXTRACTION FROM ORGANIC WASTE

BACKGROUND OF THE INVENTION

The process of extracting methane gas from carbon compound bearing material such as animal waste by anaerobic bacterial digestion is well known and has received considerable, recent attention because of the energy crisis. As a source of fuel gas and fertilizer the process has attraction both for small, farm unit operation and larger feedlot applications where ground water pollution is a persistent problem.

In a conventional application livestock waste is collected and diluted with water to form a slurry. The slurry is pumped into an air-tight container or digester. The slurry in the digester is heated to maintain it at a temperature of the order of 37° C. and the pH is adjusted and maintained within the range of 7.5 to 8.5. Under these conditions, the process of anaerobic fermentation ultimately leads to the evolution of methane, carbon dioxide and hydrogen, with traces of other gases. A sludge, useful as fertilizer remains as a residue.

During the digestion process methane production is limited by several inhibiting factors. One of these is the gradual formation of a scum at the surface of the digesting slurry. This scum and undigested solid particles accumulated in the digester require, eventually, that the gas producing operation be halted and the digester be cleaned out. Another inhibiting factor, present initially after loading the digester is the oxygen carried in with the slurry. Until this initial oxygen is transformed to carbon dioxide by aerobic bacteria, production of methane by the anaerobic bacteria cannot start. Rapid withdrawal of this initial oxygen from the system can thus decrease the detention time of the raw material in the digester. A further and primary inhibiting factor results from the concentration of dissolved ammonia reaching a toxic level in the digester. Since urine contributes approximately two-thirds of the ammonia present in the digester slurry, conventional methane generator plants have had to exclude the nitrogen-rich urine or increase the size of the digester vessel so that the concentration of ammonia can be decreased by increased dilution with water. Both alternatives have obvious disadvantages.

Anaerobic bacterial digestion processes are disclosed in U.S. Pat. Nos. 3,383,309 and 2,198,737. These attempt to deal with the digestion inhibiting factors by introducing hydrogen gas and recycled digester gases into the slurry in the digester (U.S. Pat. No. 3,383,309) and by reducing the formation of scum through mechanically agitation of the slurry (U.S. Pat. No. 2,198,737).

The process of the present invention differs from conventional methods of methane extraction primarily in that, during the digestion process, a sub-atmospheric pressure is maintained in the digester. This provides several unexpected, efficiency-enhancing results.

As presently understood, the sub-atmospheric pressure above the slurry level in the digester vessel stimulates bacterial action by drawing gas out of the slurry as it is generated, insuring constant anaerobic fermentation and accelerated decomposition of the raw waste. The dissolved ammonia in the slurry, which slows or inhibits methane production in the conventional methane generator plant, is rapidly drawn from the slurry, as free ammonia with the methane gas. The inhibiting effect of the ammonia is thus minimized. Further the eruption of the gas from the slurry due to the accelerated rate of gas evolution tends to break up scum formation. The result is more rapid production of methane gas and makes possible a reduction in the detention time of the slurry in the digester of the order of sixty-five percent, that is, in a typical installation, a reduction from twenty-eight days to ten days. The ammonia, extracted from the output side of the system, represents a valuable by-product.

DESCRIPTION OF THE PREFERRED EMBODIMENT

Figure 1:
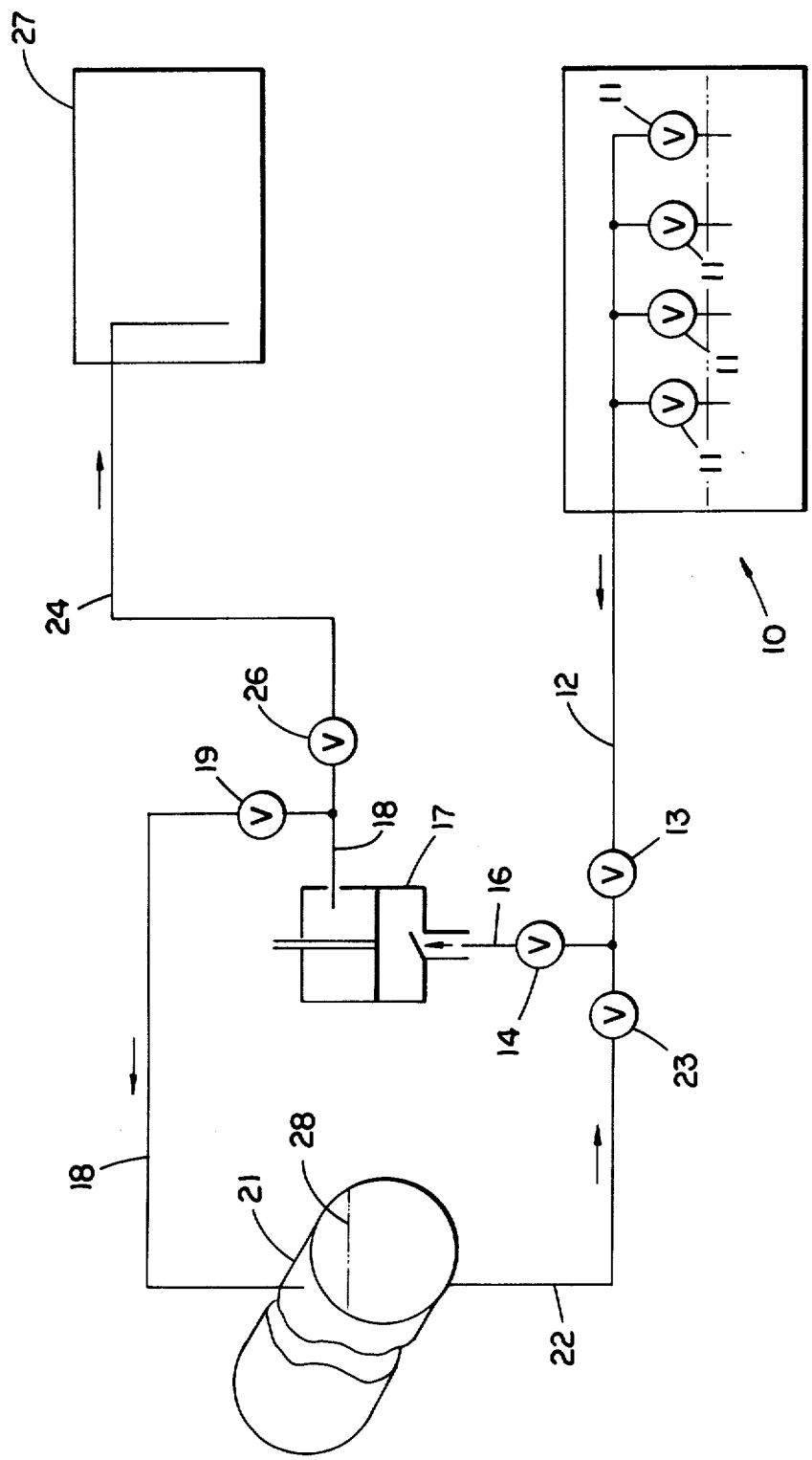
FIG. 1 is a schematic view of the interconnected components illustrating the input side of the system.
Figure 2:
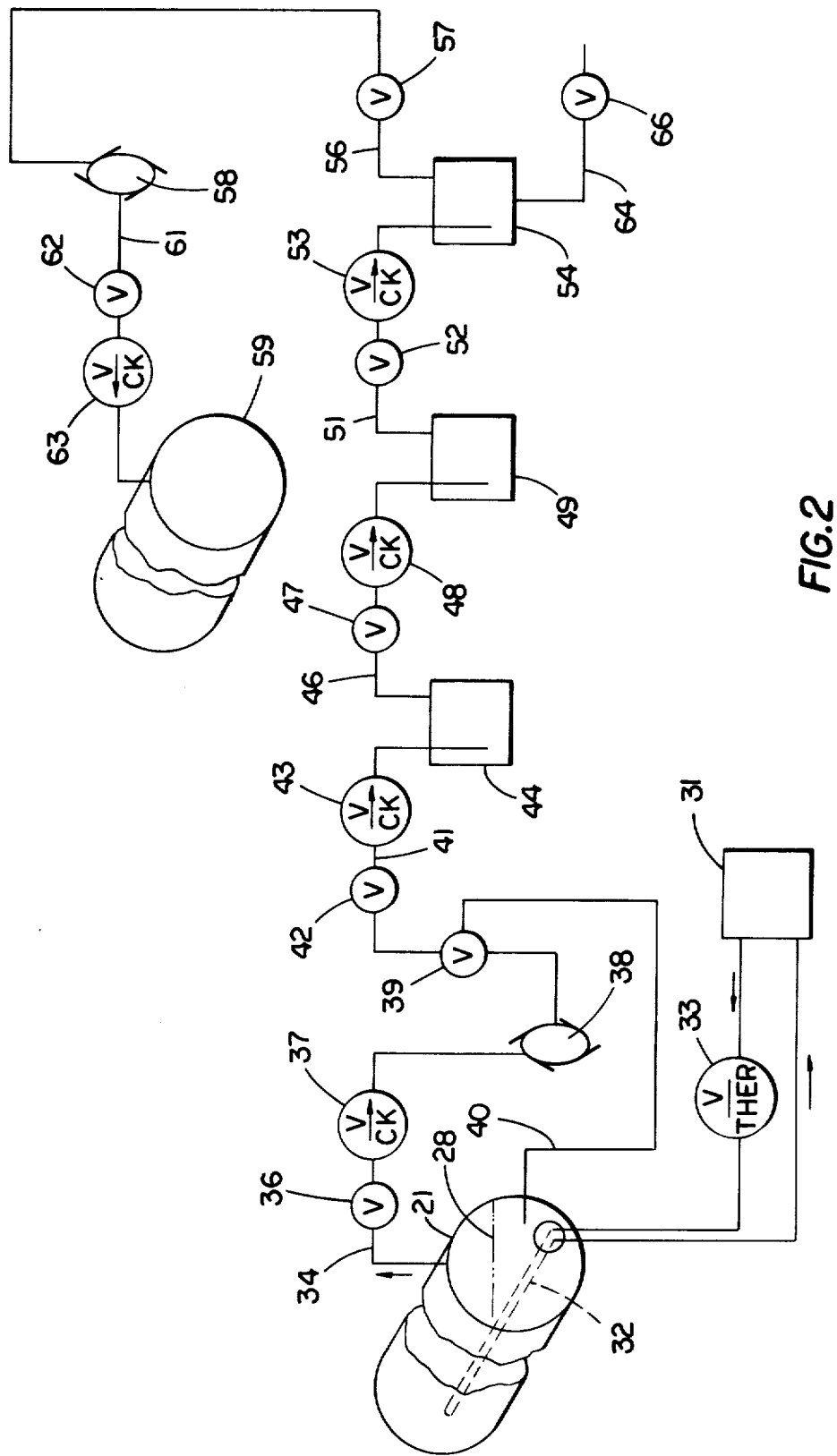
FIG. 2 is a schematic view of the interconnected components illustrating the output side of the system.

Referring initially to FIG. 1, multiple primary collection pits for holding the slurry formed by a suitable dilution of livestock manure, for example, are indicated at 10. Valves 11 permit selective withdrawal of the slurry through pipe or conduit 12. Pipe 12 communicates through valves 13 and 14 with a pipe 16 which is connected to the suction side of a diaphragm type lift pump indicated at 17. The pump is conventional and may take the form of pump Model 138ES manufactured by the Edson Co., New Bedford, Mass. The discharge side of the pump is connected to a pipe 18 which, through valve 19, extends to the upper portion of the cylindrical digester vessel 21. A draining line 22 extends from the base of the digester, through a valve 23, to the junction of pipes 13 and 16. A pipe 24 extends from pipe 18, through a valve 26 into a settling tank 27 receiving the digested sludge from the digester 21.

With one or all of the valves 11 open, maintenance valves 13, 14 and 19 open, valves 23 and 26 closed, and with pump 17 in operation, the raw slurry will be moved from collection pits 10 into the digester 21. Filling will continue until the slurry in the digester reaches the approximate level indicated at 28, that is, short of completely filling the digester. The pump 17 may, of course, be jointly controlled by appropriate slurry level responsive switches in the digester and in the pits 10 so that air does not enter the system through the pipe 12 and the digester is not over-filled.

When digestion of the slurry has been completed, by opening valves 23 and 26 and closing valves 19 and 13 the pump 17 may be operated to withdraw the residual sludge from the digester and deposit it in the settling tank 27. By closing valves 13 and 26 and opening valves 23, 14 and 17, the pump can be utilized to circulate and agitate the slurry in the digester 21. The slurry input and supply system to the digester so far described is generally conventional.

The arrangement providing the improved performance of the system will now be described with reference to FIG. 1 showing the output side of the system. A hot water boiler, indicated at 31, circulates hot water through heating coils 32 which extend into the slurry in the digester. A thermostatic valve 33, responsive to the slurry temperature, maintains the desired thermal flow to the digester so as to maintain the slurry at the desired, optimum temperature for anaerobic, methane-producing bacterial action, a temperature of the order of 37° C. having been found, at present, to be satisfactory.

Extending from the top of digester 21 is a gas conduit or pipe 34 in which a valve 36 and a check valve 37 are interposed. The pipe 34 extends to the suction side of a vacuum type dry gas compressor 38. The compressor 38 is conventional such as the Model 290-107 manufactured by the Corkin Co. of Oklahoma City, Okla. It may be controlled by a pressure sensor or pressure switch in the digester so as to maintain a subatmospheric pressure above the slurry level in the digester. A pressure in the digester in the range of 67.06 to 201.18 mm mercury (Hg) gage vacuum has been found to be satisfactory although the acceptable range may be extended to 22.34 to 268.08 mm mercury (Hg) gage vacuum.

The high pressure side of the compressor is connected to a three-way valve 39 and a pipe 41, having a valve 42 and a check valve 43 interposed. The third path through the valve 39 communicates with a line 40 for selectively returning some of the gas leaving the digester back to the slurry undergoing digestion. The pipe 41 extends into a conventional ammonia extractor 44 in which the gas is passed through nitric acid where the ammonia gas is precipitated out as crystalline ammonium nitrate. The extractor 44 may, of course, be arranged to provide for continuous draw-off of the precipitated ammonia compound which is a valuable by-product of the system. A pipe 46 extends through valve 47 and check valve 48 to a conventional carbon dioxide scrubber 49. The gas, having ammonia and carbon dioxide removed, then moves through a pipe 51, valve 52 and check valve 53 to a gas dryer 54. The gas dryer is preferably of the conventional ethylene glycol type a form of which is manufactured by the B & S Scrubber Co. of Evansville, Ind.

A pipe 56, with interposed valve 57 conducts the now pipe-line quality methane gas to the suction side of a conventional dry gas compressor 58. The compressor may be controlled by a pressure switch responsive to the pressure of the gas leaving the ammonia extractor 44 and functions to increase the pressure of the methane gas to an elevated value of the order of two hundred pounds per square inch for storage in tank 59. Pipe 61, in which valve 62 and check valve 63 are interposed, leads from the compressor to the storage tank 59. A line 64 controlled by a valve 66 permits draining of the gas dryer 54.

In operation, with the digester filled to operating level 28, with maintenance valves 36, 42, 47, 52, 57 and 62 open, and with three-way valve 39 positioned to provide communication between the high pressure side of compressor 38 and valve 42, compressor 38 will establish a relatively constant subatmospheric pressure in the digester. If necessary, the pH of the slurry may be adjusted by feeding back a portion of the evolved gas through line 40 to the slurry. Ammonia is removed at 44 and carbon dioxide at 49. The gas is dried at 54 and then raised in pressure and stored in tank 59. Maintaining a subatmospheric pressure in the digester results in drawing of the bacterially produced gas out of the slurry as the gas is generated and insures constant anaerobic fermentation and accelerated decomposition of the raw waste.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of extracting methane and ammonia from livestock waste material by anaerobic bacterial digestion of the material comprising the steps of providing a continuous load displacement type digester tank, forming a slurry of water and the livestock waste material, introducing the slurry into the digester tank to a predetermined level which defines a gas collection chamber in the tank above the slurry level, maintaining the slurry in the digester tank at a temperature of approximately 37° C. and at a pH within the range of 7.5 to 8.5, providing a conduit communicating with the collection chamber for withdrawing methane and ammonia generated therein by the bacterial digestion process, and maintaining said collection chamber and a portion of said conduit at a pressure within the range of 67.06 to 268.08 mm Hg gage vacuum while the digestion process proceeds.

* * * * *